June 7, 1949. J. D. BROWNELL Plant Pat. 845
ROSE PLANT
Filed April 22, 1946
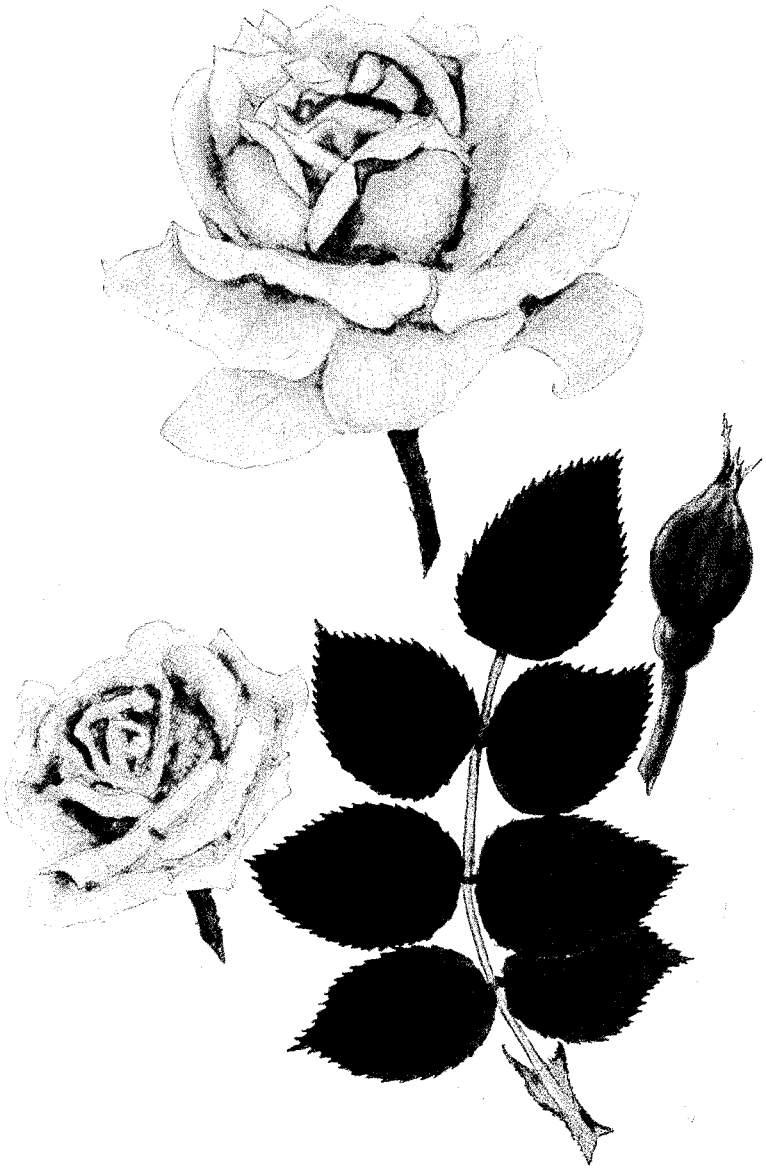
Josephine D. Brownell.
INVENTOR
BY
ATTORNEY Patented June 7, 1949

Plant Pat. 845

UNITED STATES PATENT OFFICE

845

ROSE PLANT

Josephine D. Brownell, Little Compton, R. I.

Application April 22, 1946, Serial No. 663,870

1 Claim. (Cl. 47—61)

My invention relates to roses, and especially to a new, original and distinct variety of the class known commercially as "hybrid teas" and is a variant in that class, being a *Rosa wichuraiana* hybrid tea, produced by me and under my direction in the breeding grounds of my research gardens in Little Compton, Rhode Island, by propagation, selection, and cross pollenation, which can be and has been asexually reproduced.

My new rose is new as to the following characteristics and especially as to their joint association with the characteristics inherited from *Rosa wichuraiana,* of hardiness or immunity from serious injury on account of cold temperatures prevailing in certain parts of the northern United States:

The red shades (ordinary dictionary definition) of its petals, the unusual brilliance and luster thereof and their tendency to hold these colors under exposure;

The novelty and variation within certain definite limits of the form of the bloom, its character of holding that form for a long time and the large size of the flowers;

Its character of fragrance;

Its remontant and everblooming or reblooming habit;

Its unusual abundance of petals;

Its unusual abundance of flowers, notably after early bloom time until frost;

Its character of ascending in height by recurrent branching.

In the accompanying drawing forming a part of this specification I have shown my new rose in its natural colors, that is, as near as is possible to do so artificially. As the plant develops in growth many of the leaflets mature in size to about twice the relative size as shown in the drawing. A seven leafleted leaf is shown as this frequently occurs on my new rose plant and frequently on flower stems of descendants of *Rosa wichuraiana,* but seldom on other hybrid teas. The bud, blooms and leaf are drawn to the same scale.

My new rose plant is otherwise described as follows:

*Essential information*

Type: Hybrid tea, *Rosa wichuraiana* hybrid, dwarf to ascending to tall for garden display, cut flower and pot forcing.

Class: Hybrid tea crossed with *Rosa wichuraiana.*

Breeding or discovery: This rose plant was bred by me and under my directions by propagation and cross pollenation. It is a seedling grown from a seed produced on the variety Pink Princess, Plant Patent Number 459; this seed was produced by fertilization with pollen of Crimson Glory, Plant Patent 105.

This pollenation as well as the one that produced the seed parent included emasculating a flower and placing thereon a bag as protection from foreign and self pollen. This bag was later removed and the flower was hand pollenated with a camel's hair brush and the bag immediately replaced.

The date of this pollen cross was June 30, 1943.[1]

The seed was planted December 20, 1943, and the date of the first flower was July 10, 1944.

The plant and flower seemed to me to be of unusual merit and I have since made and directed extensive propagations and tests thereof.

Plants of this variety budded from this seedling on *Rosa multiflora* root stock, have after being entirely exposed to moderate subzero temperatures, survived and bloomed normally the following season in the hybrid tea manner. The variety has been propagated by budding at Little Compton, Rhode Island, in the months of July and August in 1944–45 inclusive and the characters have successively reproduced, true to the original seedling.

*Flower*

Habit: It blooms outdoors in Little Compton, Rhode Island, beginning about three days prior to the average beginning time of commercial hybrid teas and continues relatively to the growth of the plant until frost.

Flowers borne: Often one, frequently two or three and sometimes more on each stem in the hybrid tea type of cluster; pedicels and peduncles are medium in length and diameter, erect, stiff, almost smooth, free from large prickles and bristles but with a few tiny prickles to small hairs. Stems are long, notably strong, diameter large and notably rigid.

Quantity of bloom: Free, being cumulative in quantity of florescence from year to year as the plant increases in size, free flowering in mid summer.

Fragrance: Mild, pleasing China tea in combination with *Rosa wichuraiana* under favorable conditions.

Bud: Neck normal as described, opens well, being little affected by hot or wet weather or

[1] This and other dates herein are approximate.

both, as to color and form, except at very high temperatures the color is less intense and the form of the petals is less recurled.

Before the calyx breaks the size is medium, form pointed to ovoid, frequently with one or more sepals with foliaceous parts extending beyond the apex in some buds as much as one-half inch, the number and size of the foliaceous appendanges being variable and frequently having one narrow, pointed serrate appendange on each side of the sepals, otherwise the sepals are usually normal and regular, tapering to nearly lanceolate near the apex. Under vigorous growth an occasional bud has a sixth sepal which usually overlaps in part one of the normal sepals.

Color of the bud as the calyx opens, varies somewhat, dependent upon environment, from Carmine [1] to Bordeau. This color combination extends throughout all of the petals.

Bloom: The flower is usually 4 to 5½ inches in diameter when fully open, infrequently more or less; very double having petals variable in number usually from fifty to sixty with some narrow petals and petaloids in the center variable in number. The flower opens slowly, high centered, recurled, usually showing stamens at late maturity. The petals are variable from obovate to ovate with inner petals of narrow irregular variable forms, outer and intermediate petals recurl outward, frequently notched once at the outer apex. Texture is medium to thick and leathery, both sides satiny to shiny.

Color of opening flower and of the open flower is as described under bud and slowly changes to Rose Red and later to Rose color. The petals are substantial and after about five days drop off cleanly. The flower does not "ball" in wet weather at Little Compton, Rhode Island. The flower lasts well, is not affected at any stage by moderate cold or hot temperatures or humidity or moderate weather.

Reproductive organs:

*Stamens,* quantity medium, of slightly uneven medium length.

*Anthers,* nearly Grenadine Pink.

*Filaments,* nearly Mustard Yellow.

*Pistils* are several, of slightly uneven length, about ½ inch long.

*Styles* are Chalcedony Yellow.

*Stigmas* are Citron Yellow, the pollen is moderate in quantity.

*Ovaries* are usually all enclosed, occasionally one or more protrude.

*Hips,* form globular, color nearly like under side of leaves with variable overlay on the side exposed to the sun, smooth, walls moderately thin, fleshy.

*Sepals* are persistent.

*Seeds* variable, no germination yet noted.

*Plant*

Foliage: Is abundant to normal of compound leaves usually of three or five leaflets near the flower, five and frequently seven leafleted leaves in the middle and lower down on the stem. Size of leaflets, variable from medium small to medium hybrid tea size. The accompanying picture shows relatively the smaller sizes of leaflets. Form of leaflets

[1] Color references unless otherwise specified are to Robert Ridgway, Color Standards.

usually ovate with apex moderately acute, somewhat variable to wider and narrower, base rounded on short petiolules; margins slightly irregularly serrated by medium sized and pointed serrations. Color of the leaflets grown at Little Compton, Rhode Island is upper side Medium Dark Green to Forest Green, under side Bice Green with a variable shading of Dahlia Carmine on the serrate edges and along the ribs.

The rachises are medium with minute hairs on the edges and variable prickles on the under side, colors relatively comparable with that of leaves.

The stipules are medium long, varying around ¾ inch in length and medium width, with normal points that spread in relation to each other slightly more than 90 degrees. The edges are minutely hairy.

Stems are medium to large and when well grown and established after several years are often notably large, and grow much larger as branches extend from them. The bark is nearly Bice Green, variable, overlaid slightly with Dahlia Carmine. The prickles are nearly Dahlia Carmine and slightly variable in color turning to lighter and losing their color. Form of prickles is sharp pointed and nearly straight. Size averages about ⅜ inch.

Disease, moderately free from defoliation on account of mildew and blackspot.

Growth: Habit, dwarf becoming bushy. The growth is moderately free at first, developing each year thereafter under favorable vegetative opportunity into a larger bush by cumulative growth, by branching and stems or canes from the base, to tall bush or climbing habit.

Winter resistance: One of the notable characters of my new rose is its resistance to moderate subzero temperatures in combination with its hybrid tea type and its *Rosa wichuraiana* ancestry. This variety budded with bud entirely exposed above ground to temperatures of moderate sub-zero Fahrenheit at Little Compton, Rhode Island, survived and bloomed normally the following season. This plant so exposed to such subzero temperatures is affected thereby to the extent of at least a part of the stems and branches being injured and killed back.

Comparisons: The flower is more nearly like the flower of the old fashioned Bourbon Red varieties of extreme doubleness, except that it does not quarter its petals as it opens. In comparison with other hybrid tea roses known to me, it is differentiated by having more petals than other red hybrid teas, by being a more vigorous plant that can produce when established more flowers, has frequently seven leaflets, a distinctive resistance to winter exposure and cumulative growth from year to year, with winter survival.

I distinguish my new rose variety from that of the application No. 663,868 in part as follows: the stems of my new rose variety normally grow at an angle of about 5 degrees in relation to the gravitational influence, the stems of the other variety normally grow at an angle of about 45 degrees in relation to the gravitational influence. The petals develop more recurl and open with their surfaces more irregularly warped and not so much folded on an axis from the center of the base to the tips. The foliage without control is more susceptible to defoliation by blackspot but responds effectively to the conventional forms of control.

The branching habit of my new rose variety is unusual in that many of the long branches develop from the top eyes of stems, as high up on the stem as the base of the peduncle and the next lower two or three eyes, give the plant an unusual upright effect.

My new rose variety is different from that of application 663,871, in that it is very much darker in color and has very many more petals, that are more informally warped, and emit a fragrance more nearly like that of the damask rose and not at all like that of the carnation as does the other rose variety.

I claim:

The variety of rose plant substantially as shown and described, characterized by its resistance to winter injury, its continuity and intensity of florescence, its pleasing fragrance, its long keeping character, the form of its petals, its character of long holding its flower form, the unique color combinations of red, its large number of petals, all in association with its habit of branching and cumulative growth, from the base by stems or canes.

JOSEPHINE D. BROWNELL.

No references cited.